United States Patent [19]
Thiem et al.

[11] Patent Number: 6,058,788
[45] Date of Patent: May 9, 2000

[54] DRIVE DEVICE FOR AN AUTOMATIC EMBEDDING MACHINE FOR TREATING SAMPLES FOR HISTOLOGICAL EXAMINATIONS

[75] Inventors: Stefan Thiem, Heidelberg; Bernd Guenther, Bruehl, both of Germany

[73] Assignee: Leica Instruments GmbH, Nussloch, Germany

[21] Appl. No.: 08/974,236

[22] Filed: Nov. 19, 1997

[30] Foreign Application Priority Data

Nov. 19, 1996 [DE] Germany .............................. 196 47 662

[51] Int. Cl.⁷ ...................................................... G01N 1/00
[52] U.S. Cl. .............................................. 73/863; 422/101
[58] Field of Search ............................ 73/863; 74/22 R; 250/328; 435/30, 40.52; 436/63; 422/99, 101

[56] References Cited

U.S. PATENT DOCUMENTS

| | | |
|---|---|---|
| 3,809,897 | 5/1974 | Thomas et al. ......................... 250/288 |
| 4,557,903 | 12/1985 | McCormick . | |

FOREIGN PATENT DOCUMENTS

| | | |
|---|---|---|
| 878871 | 6/1953 | Germany . |
| 1 038 795 | 9/1958 | Germany . |
| 1 097 164 | 1/1961 | Germany . |
| 1 114 338 | 9/1961 | Germany . |
| 36 25 695 | 2/1988 | Germany . |
| 0697215 | 9/1953 | United Kingdom . |
| 0788922 | 1/1958 | United Kingdom . |
| 1083511 | 9/1967 | United Kingdom . |
| 1405940 | 9/1975 | United Kingdom . |
| 2163568 | 2/1986 | United Kingdom . |

OTHER PUBLICATIONS

"Jung Histokinette", *Leica Instruments GmbH*, Oct. 1994.
"Histokinette 2000 Manual", *Cambridge Instruments*, 1988.

*Primary Examiner*—Robert Raevis
*Attorney, Agent, or Firm*—Foley & Lardner

[57] ABSTRACT

A description is given of a drive device for an automatic embedding machine (1) for treating samples (17) for histological examinations, having a plurality of containers (4, 5) which are arranged one beside the other and are each assigned an object holder (6). The object holders (6) are fastened, on a lifting device (18), over the containers (4, 5), the lifting device (18) having a turntable (7) and a rotatably mounted guide rod (8). The guide rod (8) is designed such that it can be moved by a motor, perpendicularly with respect to the direction of rotation of the turntable (7), via the lifting device (18). Provided for the purpose of driving the guide rod (8) is an open-ended, flexibly designed drive element (21) which, at its first end, is arranged between two rollers (26, 27) of the motor drive (20) and, by means of its second end, is connected fixedly to the housing (24) of the automatic embedding machine (1). The second end of the drive element (21) is guided over a deflection roller (19) and forms a loop (28) for receiving the guide rod (8).

13 Claims, 4 Drawing Sheets

DRIVE DEVICE FOR AN AUTOMATIC EMBEDDING MACHINE FOR TREATING SAMPLES FOR HISTOLOGICAL EXAMINATIONS

BACKGROUND OF THE INVENTION

The present invention relates to a drive device for an automatic embedding machine for treating samples for histological examinations.

The preparation of tissue samples for histological examinations is carried out by a number of chemical treatments, and the samples are finally embedded in paraffin. For the chemical treatment, the water contained in the sample is first of all withdrawn from the latter and replaced by stabilizers, dyes and the like. Finally, the sample is embedded in paraffin. This means that the paraffin block can be retained in a stable manner in a receiving means of a microtome. So-called automatic embedding machines, which transport the samples automatically to the various treatment stages, have been developed for the various, successive process steps.

DE-B 11 14 338, DE-B 10 97 164, B 10 38 795 and German Patent Specification 878,871 each disclose an automatic embedding machine which is intended for treating samples for histological examinations and in which a plurality of containers arranged one beside the other are provided. The automatic embedding machines also have a plurality of object holders which are fastened, on a lifting device, over the containers. For preparation of the samples, the object holders are immersed into the respective containers via the lifting device. For this purpose, the lifting device has a turntable and a rotatably mounted guide rod.

U.S. Pat. No. 3,809,897 discloses an automatically operating sample-changing machine which is intended for a spectrometer and in which the samples can be changed via a motor-driven cable pull.

DE-A 36 25 695 discloses an apparatus which is intended for cryogenically fixing samples and in which an injector rod with the sample is prevented from rebounding elastically from a low-temperature metal mirror. For this purpose, the longitudinally movable injector rod is connected to a freewheel via a rack and a gear wheel. Once the sample has come into contact with the metal mirror, the freewheel blocks any further movement of the injector rod.

A known automatic embedding machine is described in the document "Jung HISTOKINETTE, Leica Instruments GmbH, list 6008/ND/10/94, October 1994". This automatic embedding machine contains a circular arrangement comprising a plurality of containers for the chemicals as well as heatable containers for the wax. The containers are designed to be open at the top. Provided above the containers is a rotatable plate which has a plurality of sample-receiving means and is connected fixedly to a guide rod. The sample-receiving means can be introduced into the respective containers by virtue of the plate, or the guide rod, being lowered and rotated. Once a programmable period of time has elapsed, the plate, with the sample-receiving means, is raised again, rotated by a certain amount and lowered again into the next container.

In the "HISTOKINETTE", the drive for the guide rod is realized via a motor and an associated gear mechanism. The gear mechanism has an eccentric, and the rotary movement of the latter raises the guide rod and lowers it again. The guide rod is rotated, during its downward movement, by a geared connection to a plurality of linkages. The "HISTOKINETTE" automatic embedding machine has proved successful in practice.

Throughout the process, which lasts a number of hours, the automatic embedding machine generally operates without supervision. In the event of a power failure, there is a risk of the automatic embedding machine stopping midway through operation. If it comes to a standstill during a lifting movement, the ambient air renders those samples which are being processed completely unusable since the geared drive connection of the HISTOKINETTE cannot lower the samples without power.

SUMMARY OF THE INVENTION

It is an object of the invention to overcome the aforementioned limitations which characterized prior automatic embedding machines.

It is a further object of the present invention to provide an improved automatic embedding machine in which samples can be lowered into associated containers without power.

These objects and others are achieved according to the invention by a drive device for an automatic embedding machine having a plurality of containers which are arranged one beside the other and are each associated with at least one object holder. The object holders are fastened on a lifting device over the containers, the lifting device having a turntable and a rotatably mounted guide rod. The guide rod is designed so that it can be moved by a motor, perpendicularly with respect to the direction of rotation of the turntable via the lifting device. The drive device comprises an open ended flexible drive element which is arranged at a first end between two rollers of the motor and is connected fixably at a second end to a housing of the automatic embedding machine. The second end of the drive element is guided over the deflection roller. A portion of the drive element that receives the guide rod.

According one feature of the invention, the drive element comprises a toothed belt.

According to another feature of the invention, the guide rod is mounted rotatably in the portion of the drive element that receives the guide rod.

According to still another feature of the invention, the lifting device has a rotating device which is connected to the guide rod, and the rotating device has a ball-bearing freewheel which transmits the rotary movement to the guide rod in only one direction of rotation.

According to another feature of the invention, the freewheel is associated with a latching disk with a plurality of cutouts which are arranged one beside the other.

According to yet another feature of the invention, the latching disk is connected fixedly to the guide rod.

According to still another feature of the invention, a resiliently mounted slide rod is arranged on the housing of the automatic embedding machine and the slide rod engages in one of the cutouts of the latching disk.

According to another feature of the invention, an actuating element is connected to the freewheel.

According to yet another feature of the invention, the actuating element is associated with a U-shaped wedge-type flap equipped with slopes which is arranged pivotably on the housing of the automatic embedding machine.

According to another feature of the invention, the wedge-type flap is connected to a tension spring.

According to another feature of the invention, the wedge-type flap is assigned a metal restoring plate.

According to still another feature of the invention, windings of the motor are operated in short circuit during lowering of the guide rod.

According to yet another feature of the invention, each object holder of the automatic embedding machine holds a sample for histological examination.

By virtue of the specific design of the drive device, the entire lifting/rotating mechanism, together with the sample holders, is raised, via an electric motor, into one end position as these sample holders are changed to another container. In this position, the power for the motor is switched off, and the downward movement takes place via the dead weight of the lifting/rotating mechanism. It is only during this downward movement that the rotation of the guide rod takes place, via a ball-bearing freewheel. This ensures that, irrespective of the operating state or of the position of the lifting mechanism, the samples are positively guided into the associated containers in the event of a power failure.

While a toothed belt is preferably provided as the drive element, it is also possible to use other drive elements, e.g. steel cables, flat belts and the like.

BRIEF DESCRIPTION OF THE DRAWINGS

The invention will be explained in more detail, with reference to an exemplary embodiment, with the aid of the schematic drawings, in which.

DETAILED DESCRIPTION OF THE PREFERRED EMBODIMENTS

We hereby incorporate by reference the disclosure of our German Patent Application No. 196 47 662.3-52, filed Nov. 19, 1996.

Figure 1:
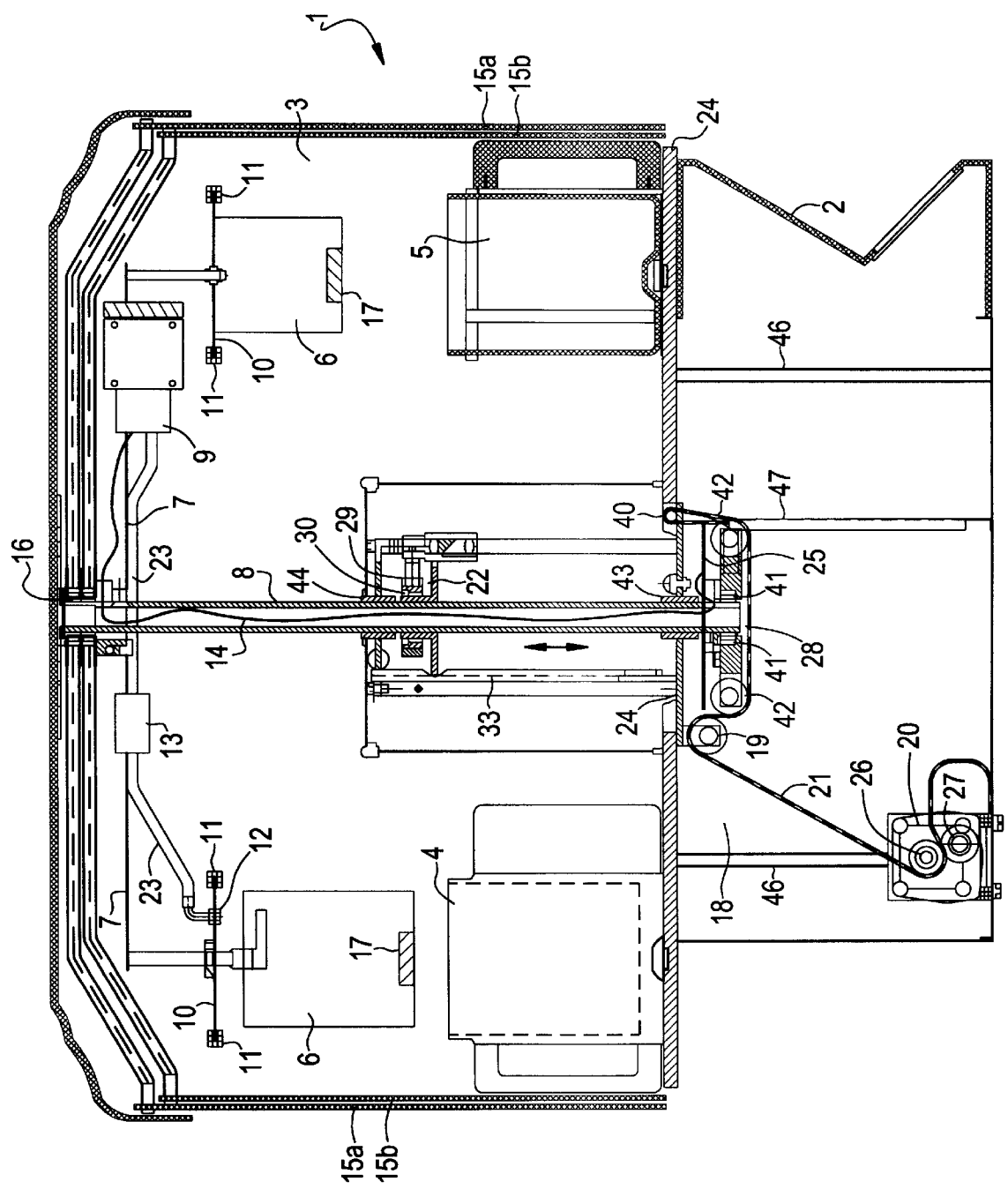
FIG. 1 is a sectional illustration of an automatic embedding machine in accordance with an embodiment of the invention.

FIG. 1 shows a sectional illustration of an automatic embedding machine 1 with a bottom housing part 2 and a top housing part 3, these two being designed to be separated from one another by a housing base 24. The housing base 24 is borne by a plurality of spacers 46. A drive device 20 for a lifting device 18, with a toothed belt 21 for a guide rod 8, is arranged in the bottom housing part 2. By virtue of the toothed belt 21 being moved via the drive motor 20, the guide rod 8 can be raised and lowered again in the direction of the double arrow. For this purpose, the drive motor 20 has a drive pinion 26 and a press-on roller 27. The first end of the toothed belt 21 runs between the pinion 26 and the press-on roller 27. A deflection roller 19 is provided on the housing base 24. The second end of the toothed belt 21 is fastened on the housing base 24 via a pin 40. Between the deflection roller 19 and the pin 40, the toothed belt 21 forms a loop 28 for receiving the guide rod 8. In particular, as illustrated, a portion of the toothed belt 21 between its second end and the deflection roller receives the guide rod 8. The guide rod 8 is mounted rotatably in the portion of the toothed belt 21 that receives the guide rod 8 via a ball bearing 41. Two further deflection rollers 42 for the toothed belt 21 are connected to the ball bearing 41.

The guide rod 8 is centered, for vertical alignment, by a bottom guide bushing 43 and a top guide bushing 44.

A slide rod 33 with a recess 49 is provided parallel to the guide rod 8. The slide rod 33 is fastened pivotably on the housing base 24.

A plurality of chemical containers 4 arranged one beside the other and a plurality of paraffin containers 5 are provided on the housing base 24. Fastened in the top region of the guide rod 8 is a turntable 7, which bears a plurality of object holders 6 with samples 17 for introduction into the respective containers 4 and 5. The object holders 6 are each equipped with a cover 10, and each cover has a peripheral seal 11.

Once the object holders 6 have been introduced into the respective containers 4, 5, the latter are closed off in an air-tight manner by the seal 11. In order to produce a vacuum in the closed-off container 4, a vacuum pump 9 is arranged on the turntable 7, and this pump is joined to a connection 12 in the cover 10 via a vacuum tube 23 and a valve 13. The vacuum pump 9 is supplied with electricity via a power cable 14 which runs in the interior of the guide rod 8. The power cable 14 terminates in the bottom housing part 2 at an electrical slipring 25 of a power supply (not illustrated).

Furthermore, a rotating device 22 with a ball-bearing freewheel 29 for the guide rod 8 is arranged in the top housing part 3. The rotating device 22 rotates the guide rod 8 by a certain angle during lowering, with the result that the object holders 6 are changed to the adjacent containers 4, 5.

For the purpose of encasing the automatic embedding machine 1, a first housing half-shell 15a and a second housing half-shell 15b are arranged at the top end of the guide rod 8. The housing half-shells 15a, 15b are arranged one inside the other and are designed such that they can be moved via a pivot bearing 16 in each case.

Figure 2:
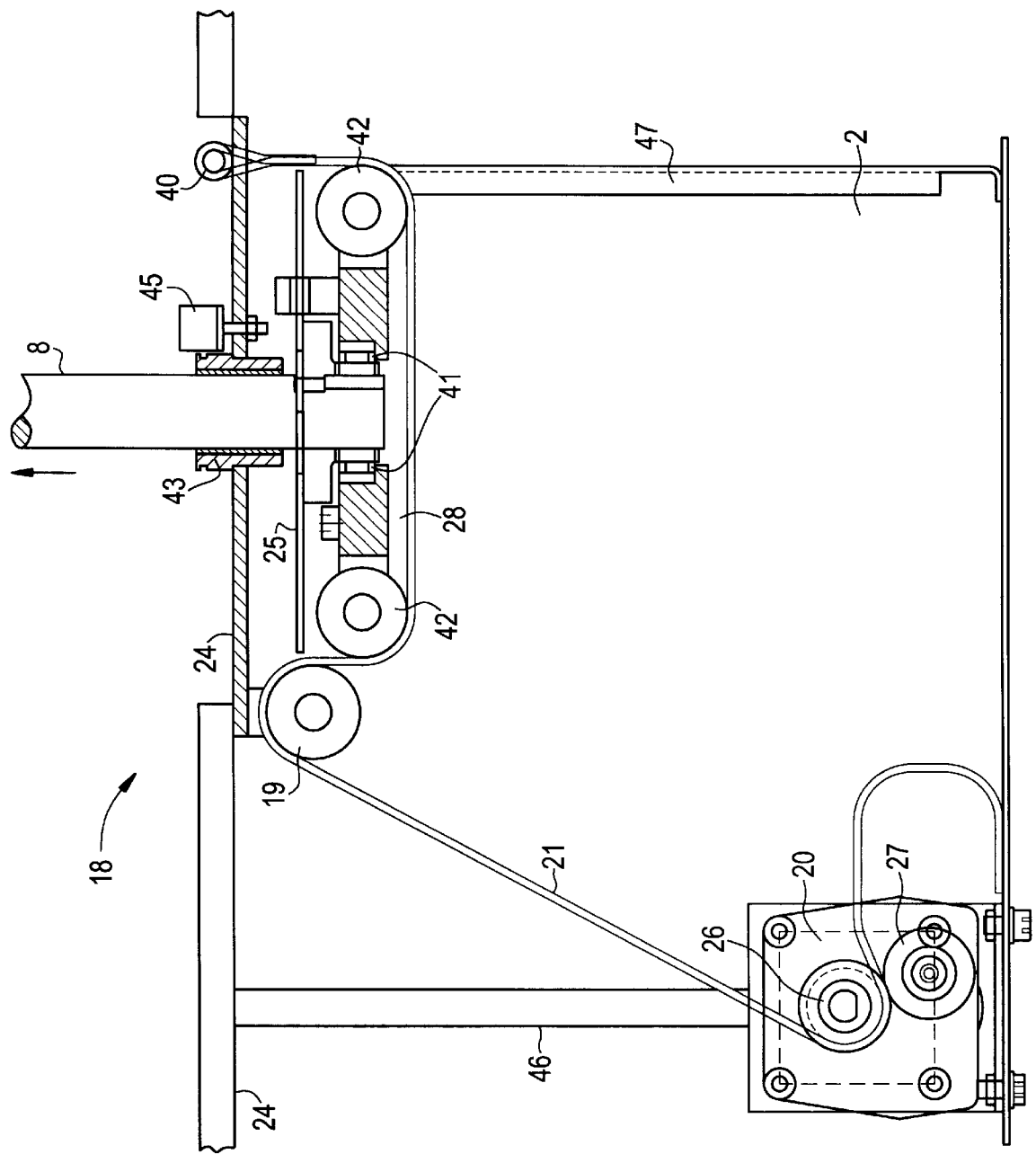
FIG. 2 is a side view illustrating in greater detail the lifting device and a drive of the embodiment of FIG. 1.

FIG. 2 is a detailed view of the lifting device 18 and the drive 20 of FIG. 1. Arranged in the bottom housing part 2 is a rule 47 for electronic detection of the position of the lifting device 18. An electronic control unit (not illustrated) can activate the motor 20 in dependence on the measured position. By drawing in the toothed belt 21 with the motor 20, the loop 28 is reduced in size and the guide rod 8 is raised in the direction of the arrow. Once one end position has been reached, measured by the rule 47, the electronic control unit operates the motor 20 in short circuit. The guide rod 8 is lowered again by its dead weight, this operation proceeding in a braked manner by the short-circuit operation of the motor 20. The end position is reached when the rotating device 22 (FIG. 1) is positioned on the buffer 45.

Figure 3:
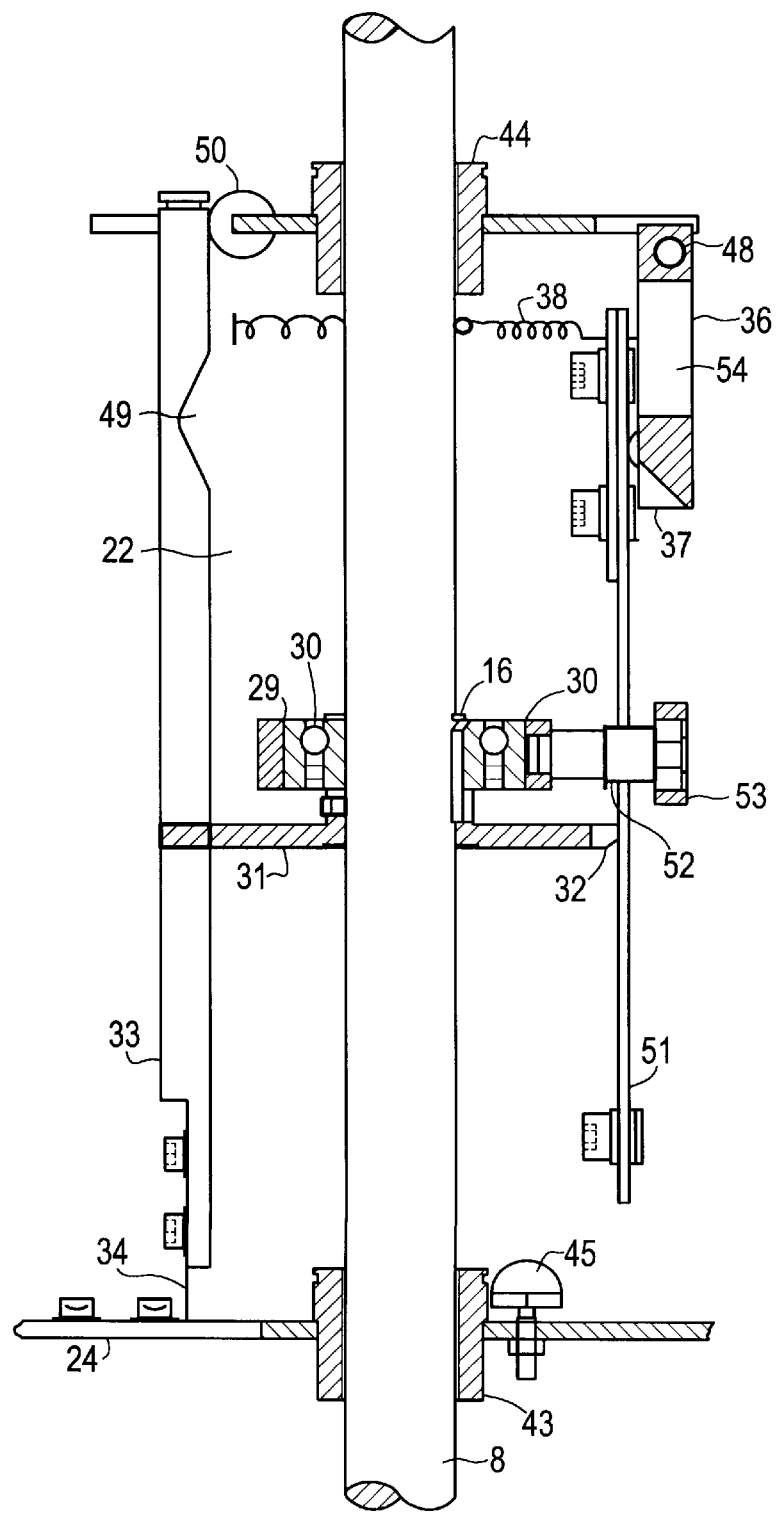
FIG. 3 is a side view illustrating in greater detail the rotation device of the embodiment of FIG. 1.

FIG. 3 is an enlarged detail view of the rotating device 22. A latching disk 31 is arranged fixedly on the guide rod 8. A ball bearing 30 of a freewheel 29 is provided over the latching disk 31. Furthermore, a pin 52, which bears a rotatably mounted ring 53, is arranged on the freewheel 29. By virtue of the pin 52 being pivoted around the guide rod 8, this movement is transmitted to the guide rod 8 via the freewheel 29. The freewheel 29 ensures that the return movement of the pin 52 does not transmit any rotary movement to the guide rod 8.

The rotary movement of the guide rod 8 is restricted by the latching disk 31, which has a plurality of cutouts 32 arranged one beside the other. The slide rod 33, mounted via the spring 34, engages in one of the cutouts 32, said rod being assigned a buffer 50 for cushioning purposes.

Arranged fixedly on the automatic embedding machine 1 is a guide plate 51 which serves for restricting the return movement of the ring 53. For this purpose, the pin 52 slides along the guide plate 51. This guide plate 51 additionally serves as a stop for a wedge-type flap 36, which is mounted on the automatic embedding machine 1 such that it can be pivoted around a pivot pin 48 in the direction of the double arrow. The wedge-type flap 36 is equipped with slopes 37. Arranged on the wedge-type flap 36 is a spring 38, the other end of which is connected to the automatic embedding machine 1.

During the upward movement of the guide rod 8, the wedge-type flap 36 is pivoted out to the right via the ring 53. In the process, the spring 38 is tensioned. As the upward movement of the guide rod 8 continues, the ring 53 slides into a U-shaped recess 54 of the wedge-type flap 36. Drawn by the spring 38, the wedge-type flap 36 is moved in the direction of the guide plate 51 and is located in its initial position (illustrated) again. Upon completion of this movement of the wedge-type flap 36, the lifting movement of the guide rod 8 terminates and the motor 20 is switched off, and the motor windings are operated in short circuit.

Figure 4:
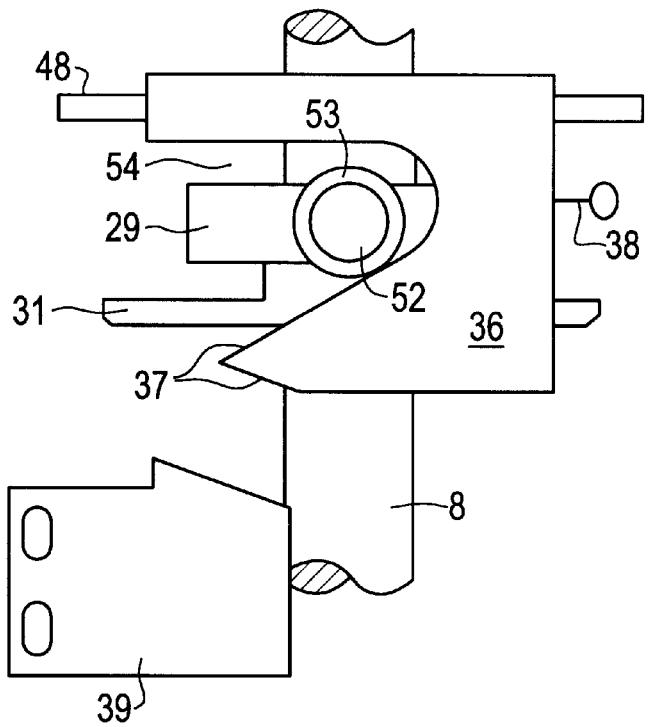
FIG. 4 shows a position of a wedge-type flap during the downward movement of the guide rod in accordance with an embodiment of the invention.

FIG. 4 is a detailed view showing the wedge-type flap 36 pivoted in, during the downward movement of the guide rod 8. The ring 53 is positively guided via the slope 37 in the U-shaped recess 54. This positive guidance transmits the resulting movement of the ring 53 to the freewheel 29 via the pin. The freewheel 29 rotates the guide rod 8. For the purpose of returning the ring 53 into its initial position, a metal restoring plate 39 is provided on the automatic embedding machine 1, and the ring 53 runs off this plate.

Figure 5:
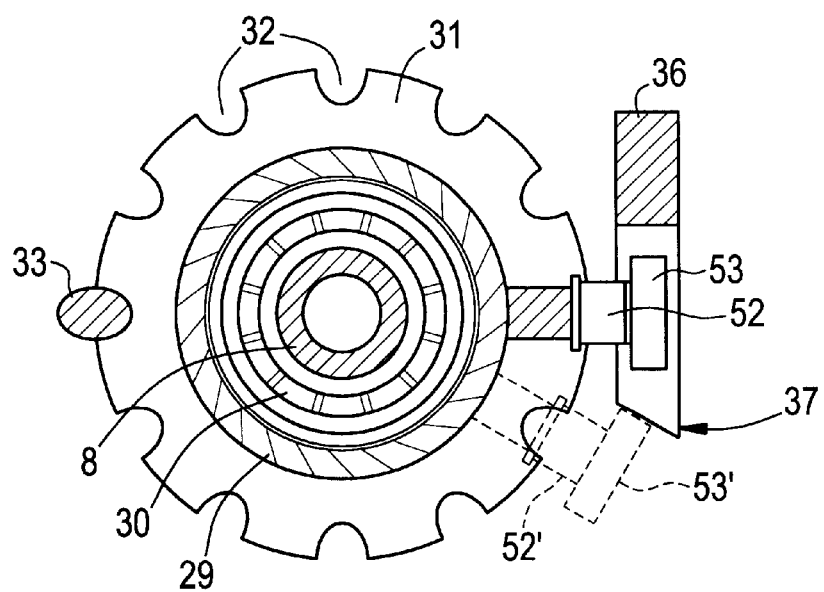
FIG. 5 is a plan view of a latching disk with the wedge-type flap and the guide rod of the embodiment of FIG. 4.

FIG. 5 is a plan view of the latching disk 31 with the cutouts 32 arranged one beside the other. The slide rod 33 engages in one of the cutouts 32. The freewheel 29 is connected to the ring 53 via the pin 52, said ring running off the wedge-type flap 36. The dashed-line ring 53' and the pin 52' show the position of the ring once it has run off the wedge-type flap 36.

In this position, the slide rod 33 is introduced into one of the cutouts 32 of the latching disk 31 again, in order to prevent further rotation of the guide rod 8. The latching disk 31 and the guide rod 33 secure the guide rod 8 against unintentional rotation. It is merely when the ring 53 runs off the wedge-type flap 36 that the slide rod 33 is disengaged by way of its recess 49 (FIG. 3). Upon termination of the rotation of the guide rod 8, the slide rod latches immediately in an adjacent recess 32 of the latching disk 31.

The invention has now been described in fulfillment of the foregoing objects by reference to a preferred embodiment. Various other embodiments and modifications will also be apparent to those skilled in the art without departing from the spirit and scope of the invention.

What is claimed is:

1. A drive device for an automatic embedding machine having a plurality of containers which are arranged one beside the other and are each associated with at least one object holder, the at least one object holder being fastened on a lifting device over the containers, the lifting device having a turntable and a rotatably mounted guide rod, and the guide rod being moveable by a motor perpendicularly with respect to the direction of rotation of the turntable via the lifting device, the drive device comprising:

an open-ended, flexible drive element which is arranged at a first end between two rollers of the motor and is connected fixedly at a second end to a housing of the automatic embedding machine, the second end of the drive element being guided over a deflection roller wherein a portion of the drive element between the second end and the deflection roller receives the guide rod.

2. The drive device for an automatic embedding machine as claimed in claim 1, wherein the drive element comprises a toothed belt.

3. The drive device for an automatic embedding machine as claimed in claim 1, wherein the guide rod is mounted rotatably to the drive element.

4. The drive device for an automatic embedding machine as claimed in claim 1, wherein the lifting device has a rotating device which is connected to the guide rod, and the rotating device has a ball-bearing freewheel, which transmits the rotary movement to the guide rod in only one direction of rotation.

5. The drive device for an automatic embedding machine as claimed in claim 4, wherein the freewheel is associated with a latching disk with a plurality of cutouts which are arranged one beside the other.

6. The drive device for an automatic embedding machine as claimed in claim 5, wherein the latching disk is connected fixedly to the guide rod.

7. The drive device for an automatic embedding machine as claimed in claim 6, wherein there is arranged on the housing of the automatic embedding machine a resiliently mounted slide rod which engages in one of the cutouts of the latching disk.

8. The drive device for an automatic embedding machine as claimed in at least one of claims 4, wherein an actuating element is connected to the freewheel.

9. The drive device for an automatic embedding machine as claimed in claim 8, wherein the actuating element is associated with a U-shaped wedge-type flap equipped with slopes, and the wedge-type flap is arranged pivotably on the housing of the automatic embedding machine.

10. The drive device for an automatic embedding machine as claimed in claim 9, wherein the wedge-type flap is connected to a tension spring.

11. The drive device for an automatic embedding machine as claimed in claim 9, wherein the wedge-type flap is associated with a metal restoring plate.

12. The drive device for an automatic embedding machine as claimed in claim 1, wherein windings of the motor are operated in short circuit during lowering of the guide rod.

13. The drive device for ant automatic embedding machine as claimed in claim 1, wherein each object holder holds a sample for histological examination.

* * * * *